(12) United States Patent
Jaffal et al.

(10) Patent No.: US 12,385,002 B1
(45) Date of Patent: Aug. 12, 2025

(54) AUTOMATED PRIMARY CELLS' TRITURATOR

(71) Applicants: Sahar M. H. Jaffal, Zarqa (JO); Maram M. H. Jaffal, Fintas (KW)

(72) Inventors: Sahar M. H. Jaffal, Zarqa (JO); Maram M. H. Jaffal, Fintas (KW)

( * ) Notice: Subject to any disclaimer, the term of this patent is extended or adjusted under 35 U.S.C. 154(b) by 876 days.

(21) Appl. No.: 17/581,400

(22) Filed: Jan. 21, 2022

(51) Int. Cl.
| | | |
|---|---|---|
| *C12M 3/00* | (2006.01) | |
| *B01L 3/00* | (2006.01) | |
| *C12M 1/12* | (2006.01) | |
| *C12M 1/33* | (2006.01) | |
| *C12M 1/36* | (2006.01) | |

(52) U.S. Cl.
CPC ............ *C12M 45/02* (2013.01); *C12M 23/54* (2013.01); *C12M 37/02* (2013.01); *C12M 41/48* (2013.01)

(58) Field of Classification Search
CPC .............................. C12M 41/48; C12M 45/02
See application file for complete search history.

(56) References Cited

U.S. PATENT DOCUMENTS

| | | | | |
|---|---|---|---|---|
| 5,691,208 A * | 11/1997 | Miltenyi | ............... | B03C 1/0332 |
| | | | | 435/7.1 |
| 9,580,678 B2 * | 2/2017 | Haun | ..................... | G01N 1/286 |
| 10,273,459 B2 * | 4/2019 | Noggle | .................. | C12M 35/02 |
| 10,287,543 B2 * | 5/2019 | Poggel | .................. | C12M 29/16 |
| 10,946,066 B2 * | 3/2021 | Rafii | .................. | A61K 38/1825 |
| 11,136,556 B2 * | 10/2021 | Noggle | .................. | C12M 41/48 |
| 2008/0187519 A1 * | 8/2008 | Sen | .......................... | C12N 5/00 |
| | | | | 435/378 |
| 2013/0330248 A1 * | 12/2013 | Shioyama | .............. | C12M 45/02 |
| | | | | 422/516 |
| 2017/0145369 A1 * | 5/2017 | Poggel | .................... | C12M 23/46 |
| 2018/0305671 A1 * | 10/2018 | Koehler | ................ | A61L 27/362 |
| 2020/0032217 A1 * | 1/2020 | Noggle | ................ | C12N 5/0696 |

(Continued)

FOREIGN PATENT DOCUMENTS

WO   WO-2017127921 A1 *   8/2017

OTHER PUBLICATIONS

Shefer et al. (2005) Isolation and culture of skeletal muscle myofibers as a means to analyze satellite cells. Methods Mol Biol. 290, pp. 281-304.*

(Continued)

*Primary Examiner* — Nathan A Bowers

(57) ABSTRACT

Extracting healthy primary cells from animals or human (e.g. aborted fetuses) is one of the challenging methods in scientific laboratories. At the same time, it is needed to conduct experiments in many fields such as neuroscience, cell biology, developmental biology, transplantation, molecular biology. Trituration is one of the steps required for the extraction of primary cells. The conduction of this challenging process needs care as if it was not done properly, it can lead to cell death or low yield. There is need for an apparatus to conduct trituration with steady force and speed (flow rate), decrease the efforts and time of researcher and allow flexibility in choosing the speed, suspension's volume and number of trituration steps. The primary cells' triturator can achieve the aforementioned properties, help in increasing the number and quality of primary cells that survive in culture and lead to decrease in the costs of the experiment.

1 Claim, 4 Drawing Sheets

Schematic diagram for the automated primary cells' triturator.

(56) References Cited

U.S. PATENT DOCUMENTS

2022/0290094 A1* 9/2022 Guest ..................... C12M 23/28
2023/0407232 A1* 12/2023 Jovanovich ....... B01L 3/502715

OTHER PUBLICATIONS

Jaffal et al. (2021) Effect of *Arbutus andrachne* L. methanolic leaf extract on TRPV1 function: Experimental and molecular docking studies. Journal of Applied Pharmaceutical Science vol. 12(10), pp. 69-77.*

Ray et al. (2014) Human primary mixed brain cultures: Preparation, differentiation, characterization and application to neuroscience research. Molecular Brain, 7:63.*

* cited by examiner

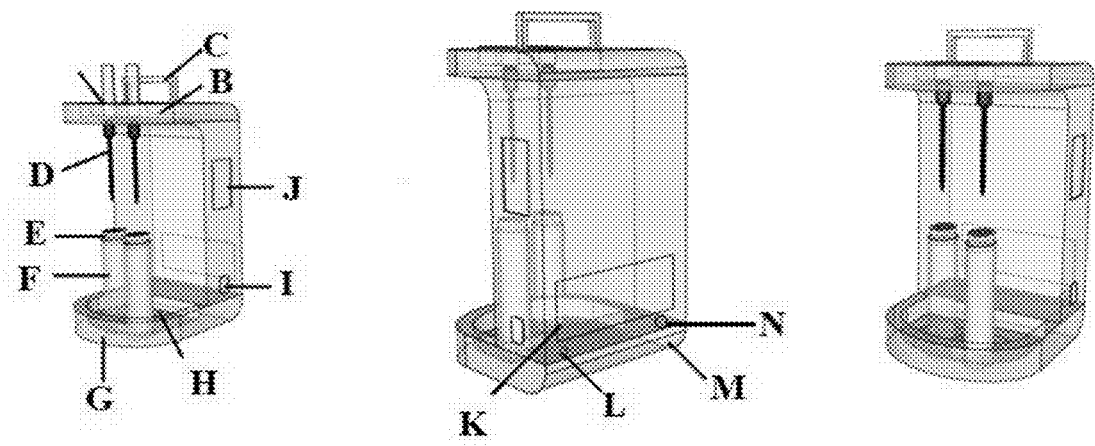
Figure 1: Schematic diagram for the automated primary cells' triturator.
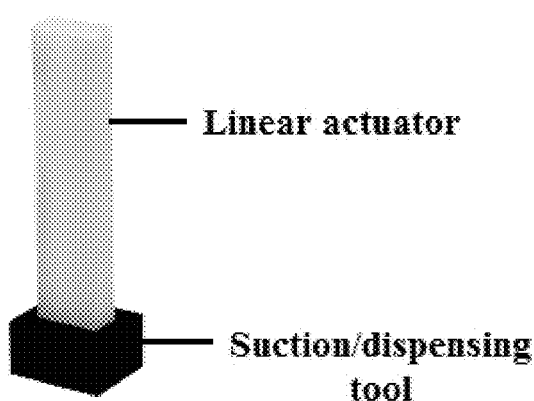
Figure 2: The suction tool that is built in at the top part of the triturator.

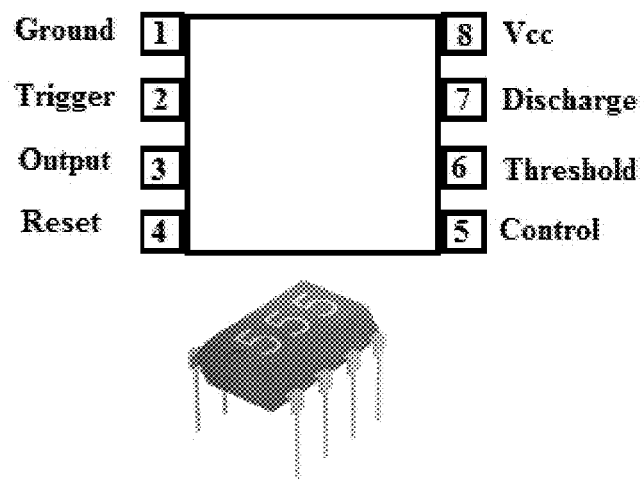
Figure 3: An illustration for the PWM high current motor speed controller (IC 555).
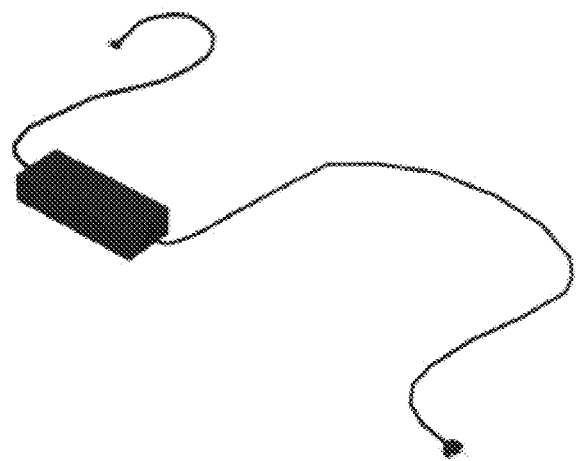
Figure 4: The charger for the battery of the automated primary cells' triturator.

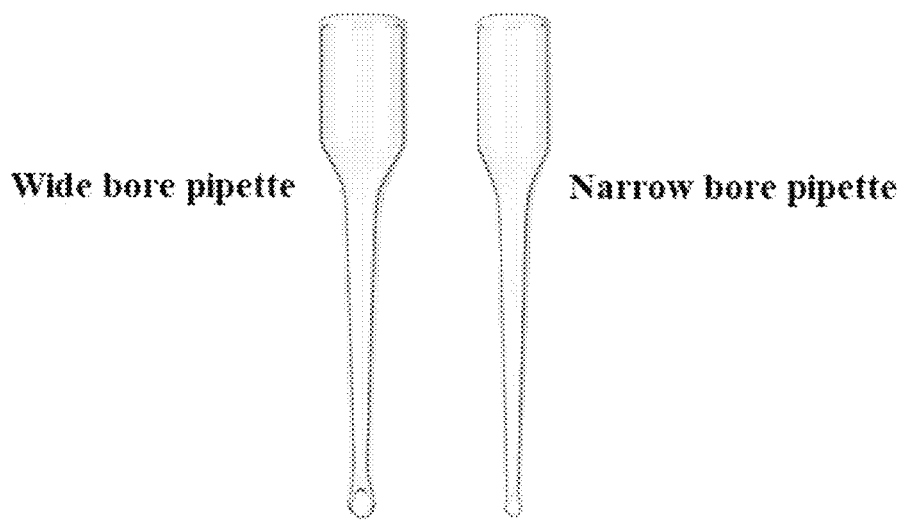
Figure 5: The wide bore and narrow bore pipettes in the automated primary cells' triturator.
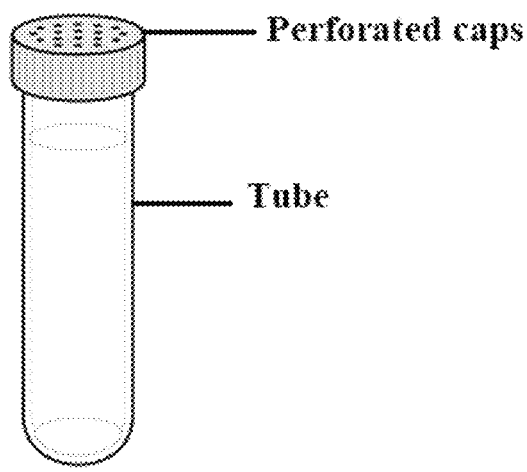
Figure 6: The tube with perforated caps used in the automated primary cells' triturator.

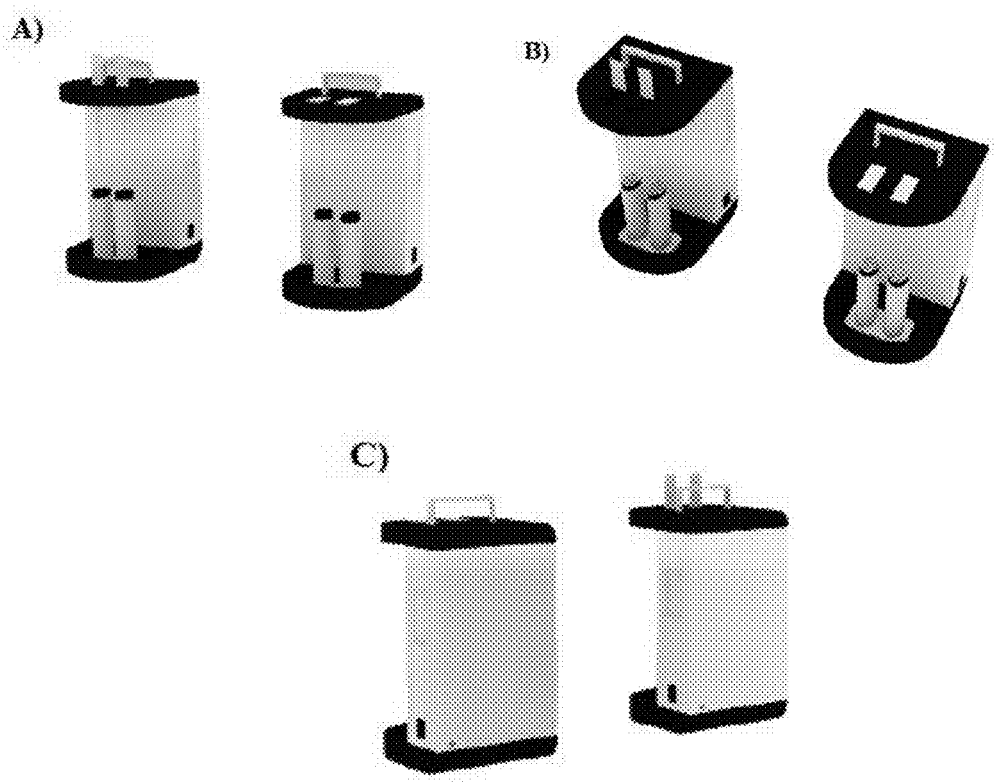
Figure 7: represents a general design for the automated primary cells' triturator (A: Front view; B: Top view; C: Back view).

AUTOMATED PRIMARY CELLS' TRITURATOR

CROSS-REFERENCE TO RELATED APPLICATIONS

This application claims what is mentioned in the current non-provisional application. There is no previous application.

FIELD OF THE INVENTION

The invention is related to an automated primary cells' triturator used to isolate primary cells with fixed steady speed and flexibility to choose the speed, suspension's volume and number of triturations that can be done in the experiment, according to the used experimental protocol which depends on the type of cells to be extracted.

The device is useful in several scientific fields including, but not limited to, neuroscience, cell biology, developmental biology, transplantation and molecular biology.

OBJECT OF THE INVENTION (AUTOMATED PRIMARY CELLS' TRITURATOR) & THE PROBLEMS THAT THE INVENTION SOLVES

The primary cells' triturator is designed to enhance the extraction of primary cells such as dorsal root ganglia (DRG) neurons from embryos and adult animals.

The primary cells' triturator is designed to enhance the dissociation of primary cells from tissues using fixed steady speed and pipettes with variable bore sizes to increase the survival of isolated cells.

BACKGROUND OF THE INVENTION

According to the present invention, the term "primary cells" encompasses ex vivo cell populations that are directly derived from tissues while the term "solution" refers to a uniform mixture where substances are dissolved in a liquid, commonly used to support cell growth or to assist in the extraction and handling of biological tissues.

According to the present invention, the term "trituration" includes the mechanical dissociation of primary cells through aspiring and dispensing the solution that contains tissues after digesting these tissues with enzymes used to break down the connective tissues.

According to the present invention, the term "dissociate or dissociation" refers to separating cells.

According to the present invention, the term "speed or flow rate" refers to the volume of solution that is aspirated or dispensed in a unit of time.

In the experiments that lead to clinical trials or drug development, it is important to use mammalian cells that can be extracted from animals or human to avoid the variations that may arise in the in vivo experiments (e.g. stress). The use of these cells is also important in cloning, gene expression, production of monoclonal antibodies and recombinant proteins.

Importantly, the isolation of primary cells is required in a field like neuroscience for culturing neurons and conducting experiments ee using them.

Furthermore, isolating primary cells from specimens that are taken from cancer patients is useful in studying the responsiveness of tumor cells to hormones and chemotherapy.

Thus, the successful isolation of healthy primary cells is a crucial aspect in several fields of science.

Notably, the use of primary cells that are cultured immediately from mammalian cells has benefits over the cells that are cultured for long time whereby cell changes and adaptive modifications can occur.

A skilled person knows that cells need to be cultured at a suitable density in order to grow well. Worthy to mention, the isolation of primary cells needs care to avoid cell death or isolation of unhealthy cells that lead to inaccurate results that are not related to the experiment itself.

Further, culturing unhealthy cells leads to waste of materials and increase in the costs of the experiment. The costs that the researcher can lose in an experiment if the primary cells were not cultured properly are high costs related to the cost of media and the expensive supplements that are added to the media [such as nerve growth factor (NGF) and Glial cell-derived neurotrophic factor (GDNF)].

Other costs include costs of the animals, filters, materials used for extraction, constructs and antibodies.

Primary cells can be isolated by disaggregating a sample from its source (e.g. tissue). Disaggregation can be accomplished using methods known to those skilled in the art.

The aim of using these methods is to break connective tissues between cells and to disperse the tissue into a suspension of individual healthy cells without stress or death of cells.

The methods of primary cells' isolation include enzymatic digestion by treating the minced tissues with a digestive enzyme or combination of enzymes such as chymotrypsin, collagenase, trypsin, hyaluronidase, elastase, pronase, dispase, DNase and others. Moreover, chelating agents can be used in the chemical digestion of tissues.

Other method includes mechanical disaggregation (such as trituration).

Trituration refers to the mechanical dissociation of primary cells through aspiring and dispensing the solution that contains the cells after digesting tissues with enzyme (s) to break down the connective tissues.

Compared to enzymatic digestion, it produces colonies with defined sizes and decreases the cellular trauma during extraction.

The importance of using the mechanical disaggregation is that the successful isolation of primary cells requires a combination of the mechanical and the chemical digestion methods (using enzymes or chelating agents).

There are other advantages for using trituration in experiments. In more details, a specific substance or antibody can be added to the media during trituration to allow substance's loading (e.g. proteins) into the cytoplasm of cells after ripping the membranes.

Accordingly, trituration is useful in immunohistochemical and immunofluorescence studies.

Noteworthy, there are several factors that affect the isolation and extraction of primary cells such as cells' manipulation during harvesting, age and species of animal(s) used as a source of cells, genetic modifications of animals (if existed), enzymes (their type, quality, concentration, incubation period) and temperature.

Despite that, the degree of trituration is the most available limiting factor due to the multiple use of mechanical force to separate the cells, a matter that can limit the survival of cells if it was not done properly.

Notably, repetitive trituration is needed to isolate the primary cells. This process should be performed carefully and gently as the primary cells (in general) and neurons (in particular) are sensitive and fragile. The conduction of repetitive tritutation is challenging and time consuming.

Also, trituration is laborious and exhausting to the researcher as there is need to conduct 150 trituration step or more in some protocols [e.g. some of the protocols of used to extract DRG neurons].

Additionally, the manual creation of flame-polished pipettes to be used in produces inaccurate bore diameters and accordingly, leads to throwing or wasting pipettes that don't have suitable bore diameter.

Importantly, the variability in the force and number of trituration steps have important impact on the success of extracting cells in general (and neurons in particular). Death or low yield of cells can occur with increasing force or number of triturations. Prolonged or vigorous trituration can be very detrimental to the survival of primary cells.

To add, the trituration step should be conducted very slowly to avoid the formation of bubbles and the insertion of carbon dioxide into the media.

The successful trituration occurs when the researcher is able to dissociate the chunks of tissues and get single cells. Several beginners in research can get low yield and poor cell viability. With experience in extraction, the cell viability enhances.

Of note, the use of pipettes with fixed bore diameter is an asset as it increases the success rate of extraction. Usually, trituration can be conducted using two types of pipettes.

The first one includes a pipette with a wide bore opening and is used to dissociate the cellular connections, grossly. The second one includes a pipette with a narrow bore opening (created by polishing the pipettes using Bunsen burner to reduce the size of the opening).

For instance, the protocol of triturating DRG neurons can include 50 triturations that can be done with a wide-bore glass pipette and 100 triturations that can be done separately with a thin flame-polished glass pipette.

In fact, it is difficult to control the bore diameter of the pipette by manually polishing the pipettes with flame. Accordingly, new technology is needed to achieve the following goals:
 a) Improve the efficiency of primary cells' dissociation and at the same time maintain structural integrity, viability and survival of cells by using fixed speed during triuration.
 b) Reduce the processing time of cell dissociation from hours to minutes
 c) Use an automated system for dissociation to save the efforts of the researcher.
 d) Use a chargeable and portable system so that there is no limitation for the researcher in the workplace or in the need for electrical connection.

BRIEF SUMMARY OF THE INVENTION

The successful culture of healthy primary cells is useful for identifying the characteristics and properties of cells and determining the mechanisms that underlie different diseases. For instance, the experiments that are conducted on dopaminergic neurons are crucial in Alzheimer's research and identifying the changes in cortical neurons.

The primary cultures are used in different studies including neurodevelopmental, pharmacological, neurobiological, toxicological, transplantation and other studies.

The current invention relates to an automated primary cells' triturator that is helpful in dissociating the primary cells using a fixed speed with ability to select the speed, suspension's volume and number of triturations to be conducted.

The automated primary cells' triturator can be used in the protocols of extracting different types of primary cells such DRG neurons, dopaminergic neurons, cortical neurons, primary spheres from retina, myofibers of muscles, organoids from stem cells and other cells.

The use of the primary cells' triturator leads to the isolation of primary cells in a homogenous manner with less viability through the use of pipettes with fixed bores.

The primary cells' triturator is suitable for performing the trituration of 2 samples simultaneously to save time.

BRIEF DESCRIPTION OF THE DESIGN OF THE AUTOMATED PRIMARY CELLS' TRITURATOR AND THE RELATED DRAWINGS

FIG. 1 displays a schematic diagram for the automated primary cells' triturator.
 A represents the openings for inserting the sterile pipettes that are used for the trituration.
 B is the place of suction/dispensing tool and HEPA filter (built in the machine) that prevents the passage of fluid or contaminants to the interior of the machine.
 C represents the handle of the automated primary cells' triturator.
 D The pipettes used for trituration.
 E represents the perforated caps of the tubes.
 F represents the sterile tubes that contain media and tissues to be triturated.
 G is a drawer that can be used to keep the filters that are needed for filtering the solution after trituration, sterile tubes and other materials of the experiment.
 H is the base that is used to fix the sterile tubes during trituration.
 I represents the power switch.
 J is a digital screen (LCD display) used to set and choose the right speed (flow rate), suspensions' volume and number of triturations needed for the experiment based on the protocol.
 K is the place of the motor.
 L is the opening for inserting the charger.
 M is the place of the chargeable battery.
 N is the outlet nozzle of the apparatus.

FIG. 2 depicts a schematic illustration for the suction tool that is built in at the top part of the triturator (part B in FIG. 1)

FIG. 3 depicts an illustration for the pulse wave modulation (PWM) high current motor speed controller (IC 555).

FIG. 4 shows the charger for the battery of the automated primary cells' triturator.

FIG. 5 represents the wide bore and narrow bore pipettes in the automated primary cells' triturator.

FIG. 6 shows the tube with perforated caps used in the automated primary cells' triturator.

FIG. 7 represents a general design for the automated primary cells' triturator (A: Front view; B: Top view; C: Back view).

DETAILED DESCRIPTION OF THE INVENTION

There is no machine or product in the market that is related to the automated primary cell triturator (current invention). The previous inventions explained the importance of isolating different kinds of cells using different techniques. For example, Rafii, et al., (U.S. Pat. No. 10,946, 066) mentioned the importance of mechanical dispersing for isolating endothelial cells. The disclosure of the mentioned invention was related to methods of inducing regeneration of an organ. It is not related to the trituration process itself. Thus, the device is not designed for trituration and is not suitable for the isolation of primary cells.

In several patent publications (U.S. Ser. No. 10/273, 459B2 and U.S. Pat. No. 11,136,556B2) provided by Noggle et al., the authors depicted a system that is fundamentally directed toward the reprogramming of somatic cells, such as fibroblasts, into induced pluripotent stem cells (iPSCs), and further toward the differentiation of such reprogrammed cells into other cell types by adding growth factors to the cells and sorting the cells according to their type (hematopoetic cells, muscle cells, cartilage cells, liver cells, epithelial cells, neuronal cells and urinary tract cells). The purpose of the invention lies in automating the reprogramming and sorting of cells based on biological markers (e.g., TRA-1-60, CD13), not mechanical dissociation or tissue processing. Meanwhile, the automated primary cell triturator (the current invention) relates specifically to the isolation and mechanical dissociation of a wide range of primary cells directly from biological tissues (including, but not limited to, neurons, myocytes, and epithelial cells), thus addressing a different phase of cellular research and manipulation. The system is tailored to replicate manual trituration—a delicate and repetitive pipetting process using pipettes of defined bore sizes to achieve consistent cell dissociation without damaging the cells.

In fact, the invention proposed by Noggle et al. utilizes sophisticated biological techniques involving viral vector-based delivery of reprogramming factors, coupled with automated sorting systems for the classification and propagation of iPSC colonies, whereas the automated primary cell triturator provides a mechanical apparatus that performs precise suction and dispensing actions using pipettes of variable bore diameters to facilitate the gentle dissociation of tissues (previously treated with enzymes) into viable primary cell suspensions aiming to replace manual flame-polished pipettes with an automated, calibrated equivalent.

In more detail, the methodology employed by Noggle et al. relies on chemical and viral means, such as the use of Sendai virus vectors to initiate cellular reprogramming at the genetic level, whereas the automated primary cell triturator operates by applying controlled mechanical forces after enzymatic softening of tissues, thereby enabling dissociation of primary cells without inducing genetic changes.

Due to the use of viral vectors and reprogramming factors in the system of Noggle et al., there is an inherent risk of cytotoxicity and unwanted genomic integration that may compromise cell viability or function. By contrast, the automated primary cell triturator minimizes shear stress and mechanical trauma through the use of dual-bore pipettes and fixed flow rates, thereby preserving the physiological integrity, viability, and yield of fragile primary cells such as neurons.

While the invention of Noggle et al. describes automated liquid handling systems and reagent delivery protocols, their invention does not incorporate pipettes with different bore diameters to target sequential dissociation stages. Instead, it uses standard pipettes for reagent delivery with no specialized bore sizes. The automated primary cell triturator, however, is explicitly designed to utilize wide-bore pipettes for the initial disruption of cellular aggregates and narrow-bore pipettes for the final isolation of single cells, enabling a tiered dissociation strategy that enhances efficiency and cell survival.

The automated primary cell triturator integrates a pulse-width modulation (PWM) controller based on the IC 555 chip, which allows the operator to precisely adjust the speed (flow rate) of suction and dispensing between 6.2-50 ml/sec, a level of mechanical control absent in Noggle's et al. invention, which doesn't mention variable mechanical flow regulation tailored to cell type sensitivity.

On the other hand, the invention of Noggle et al. relies on external biosafety measures to maintain a sterile environment, not embedded filters, such as biosafety cabinets, whereas the automated primary cell triturator incorporates a built-in HEPA filter within the housing of the triturator itself, ensuring sterility at the point of cell processing.

Whereas Noggle's system automates workflows through predefined software protocols, the automated primary cell triturator equips users with an integrated LCD screen that enables real-time control and customization of experimental parameters such as the suspension's volume, the number of trituration cycles, and flow rate, while also displaying the battery level to facilitate continuous operation without power interruptions.

Noggle's system is not designed to resolve problems related to cell clumping or aggregation during the dissociation process, whereas the automated primary cell triturator targets the isolation of cells from tissues primarily and aggregation secondarily by enabling sequential and controlled mechanical dissociation, thereby increasing the likelihood of achieving a homogeneous single-cell suspension from tissue masses.

Furthermore, the automated primary cell triturator can runs two samples simultaneously compared to the invention of Noggle.

The invention of Noggle et al. is intended for use with fixed, large-scale laboratory equipment including Hamilton STARlet liquid handlers and robotic arms with liquid handlers, incubators and sorting modules, which require a stable power supply and are not portable; by contrast, the automated primary cells' triturator of the present invention is compact, lightweight, powered by a waterproof, rechargeable battery and a handle, making it uniquely suited for portable applications where electricity may not be consistently available and for a wide range of laboratory settings including sterile hoods, mobile clinics, and field stations.

While invention of Noggle et al. describes the use of complex robotic arms and modules for performing cell culture and sorting tasks in contrast to the automated primary cells' triturator simplifies the mechanical process through the use of a motorized suction and dispensing mechanism that imitates manual trituration with consistent force and timing, thereby reducing both user fatigue and procedural variability without the need for costly robotic infrastructure In another embodiment, Sen et al. (US20080187519A1) explained a chemical method for dissociating cell aggregates and not a mechanical approach for the isolation of primary cells from tissues. Also, their method is not suitable for the isolation of primary cells that are sensitive to chemical damage.

Similarly, Haun et al. (U.S. Pat. No. 9,580,678B2) proposed a microfluidic tumor tissue dissociation device. As the name of the device implies, the invention of Haun et al. employs a system that is used to dissociate solid tumors known to have three-dimensional tissue structures. As this device depends on using fluid streams for dissociation, it is not suitable for the isolation of primary cells which are fragile. In addition, no trituration control or pipette-based method was mentioned in the invention of Haun et al.

Furthermore, in the invention of Timmins et al. (WO 2017/127921A1), the inventors claimed a method of using agitated reactor for dissociating cell aggregates whereby a dissociation reagent and force are applied to dissociate cell aggregates.

The inventors described the sources of the mechanical force as the following: using impeller, stirrer, wheel, paddle, rocking, or forced fluid flow entering the agitated reactor. Based on the aforementioned explanation, the disadvantages and limitations of the invention of Timmins et al. is that it cannot be used for all types of cells particularly neurons whereby a gentle process of trituration is needed.

Additionally, there is no option to choose the number of triturations, suspension's volume or the speed of the mechanical dissociation by the user and no use for the variable bore-size pipettes or HEPA filter, thus it lacks portability.

Most importantly, the invention in the current application (automated primary cells' triturator) is related to the mechanical dissociation of individual cells from tissues and not just dispersing cell aggregates.

To add, as the use of vertical trituration is missing in the invention of Timmins et al. there is no utilization of the pipettes that have different bore diameters (wide and narrow) which are necessary in extracting primary cells from tissues.

Also, one advantage of the apparatus provided herein is that it works by electricity and a chargeable battery meaning that it can be carried to the laminar flow or the workplace to enhance the researchers' work and this feature is missing in the invention of Timmins et al.

Moreover, in several types of cells, the time used in chemical digestion is different compared to the time used in mechanical dissociation. Accordingly, it is not helpful to use a method or apparatus whereby the 2 types of digestion are used simultaneously as explained in different previous embodiments. Finally, the apparatus provided herein is used primarily for separating the cells from tissues by conducting the manual trituration separately from the enzymatic digestion to increase cell viability and not only separating cells from cell aggregates.

In other invention (Guest et al., US20220290094A1), the invention does not disclose or suggest a system for aspiration and dispensing-based trituration. In contrast, the automated primary cells' triturator addresses the pipette-based trituration using controlled mechanical components, thereby enabling reproducibility and reducing user fatigue.

The automated primary cells' triturator of this invention uniquely enables researchers to control over critical variables and set:

The volume of solution per trituration
The flow rate (speed) of aspiration and dispensing
The number of trituration cycles The invention of Guest et al. neither discloses nor suggests user-defined programmable control over these critical parameters. This feature is vital for achieving consistent dissociation without damaging fragile cells. To add, the method of Guest et al. is too harsh for applications that involve neuronal cells because it is more focused on general tissue dissociation by combining enzymatic and mechanical forces through a continuous flow system. Accordingly, the method of Guest et al. works well for processing tissues in general, but it doesn't handle the unique difficulties of triturating delicate primary cells like neurons nor provides mechanisms tailored to minimizing cellular trauma. In contrast, the automated primary cells' triturator (of this application) is tailored for fragile primary cells such as neurons, which are highly sensitive to enzymatic overexposure or uncontrolled mechanical force. The apparatus increases cell survival and yield by providing steady, gentle mechanical dissociation through regulated trituration. This makes it particularly appropriate for studies involving transplantation, neuroscience, and molecular biology and many other fields where the integrity of fragile cells is crucial.

Most importantly, trituration is a tedious, erratic, and highly technique-dependent manual process that entails repeated aspiration and dispensing at a fixed rate through pipettes. The invention of the automated primary cells' triturator automates this specific step, which is not addressed in Guest et al.'s invention.

In other aspect, the invention of Guest et al. did not use pipettes as a dissociation mechanism and didn't control the bore size of any pipette. On the other hand, the automated primary cells' triturator (of the current invention) stresses the use of sterile pipettes with known and consistent bore diameters to enable gross dissociation and single cell release. Compared to the manual flame-polishing technique that is used to produce the narrow-bore pipettes and can lead to inaccurate bore sizes, the use of pipettes with known dimensions as proposed in this invention ensures greater standardization and reproducibility-features that are absent in prior disclosures.

The invention of Guest et al. makes no reference to the portability or sterility which is a substantial benefit for research labs. The invention of Guest et al. is a benchtop, powered device in contrast to the automated primary cells' triturator outlined in the current application which is battery-operated and portable, enabling it to be used independently with a fixed power source in sterile laminar flow cabinets or other hygienic workspaces. This improves sterility and flexibility which are essential in clinical and research laboratories.

The invention of Guest et al. does not describe any capability for handling more than one sample at a time. The automated primary cells' triturator (of the current invention) allows the trituration of two samples simultaneously, doubling throughput and saving researchers considerable time, particularly in protocols involving large sample sets or parallel testing.

Additionally, the invention of Guest et al. does not use HEPA filters or sealed tools while the automated primary cells' triturator (of the current invention) focuses on sterility and contamination control. It includes HEPA filter built into the system.

The invention of Guest et al. does not use digital LCD screen for setting operational parameters compared to the automated primary cells' triturator that uses digital LCD showing the battery level and allowing researchers to choose the suspension's volume, trituration count and speed; thus enhances usability and precision.

In other embodiment (Miltenyi et al., U.S. Pat. No. 5,691,208), the invention pertains to a magnetic separation apparatus intended to isolate specific biological targets such as CD34+ hematopoietic stem cells by using antibody-magnetic binding and high-gradient magnetic fields within specially coated column matrices. Meanwhile, the automated primary cell triturator (current invention) is related to the mechanical dissociation of tissue-derived cells using enzymatic-pretreated tissue suspensions instead of magnetically labeled samples. The two principles are entirely different purpose and mechanism: magnetic for labelling specific cells versus mechanical for separating cells.

Also, the automated primary cells' triturator (of the current invention) automates the mechanical trituration of enzyme-pretreated tissue suspensions. It replicates the manual process of aspiration and dispensing through pipettes, a process commonly used in neuroscience and cell biology for the gentle dissociation of fragile primary cells. This mechanical focus is fundamentally different from the magnetic-binding employed by Miltenyi et al. Also, the use of antibody as the invention of Miltenyi et al. isn't helpful for the purpose of the current invention and is very costly.

Additionally, there is no control in the apparatus described in Miltenyi et al. over trituration steps, flow volume, or force. Oppositely, the current invention introduces programmable control over key dissociation parameters such as the number of trituration cycles, flow rate, and aspirated volume providing precision and customization of physical dissociation. Besides, the apparatus of Miltenyi et al. includes tubing system and closed columns that are not mobile or flexible (a stationary benchtop) while the automated primary cells' triturator is designed for portability, sterility, and flexibility, being battery-powered and usable within sterile laminar hoods providing control over contamination and increasing lab efficiency and throughput. These attributes enable its use directly in tissue culture workspaces—a scenario not supported by Miltenyi's et al. fixed and tubing-intensive infrastructure.

The apparatus of Miltenyi et al. uses one sample per run while the current invention handles two samples simultaneously; increasing lab efficiency and throughput.

Finally, Miltenyi's et al. invention is not suitable for the isolation of fragile primary such as neurons, for which trituration is preferred over harsh magnetic handling or filtration. The automated primary cells' triturator preserves cell viability through controlled mechanical dissociation, offering advantages in fields such as developmental neuroscience and stem cell research.

With respect to the invention of Jovanovich et al. (U.S. Pat. No. 5,691,208), there are differences from the automated primary cells' triturator (of the current invention) that addresses the challenge of automating a delicate trituration process via pipettes with fixed bore sizes that are used to extract fragile primary cells-particularly neurons from enzyme-pretreated tissue suspensions unlike the system disclosed in the invention of Jovanovich et al. which relies on enclosed mechanical agitation via blades or grinding within disposable cartridges.

While the invention of Jovanovich et al. automates bulk tissue dissociation via rotary or mechanical disruption, it does not address or offer a mechanism for precise and low-shear trituration—a critical method for preserving fragile cell morphology and viability (cell-friendly). In more detail, the use of blades is harsh for cells and causes damage to delicate cells.

The invention of Jovanovich et al. is not suitable for isolating fragile primary cells compared to the current invention which replicates the gentle aspiration and dispersing (trituration) via pipettes, a method widely used in neurobiology labs.

Further, the invention of Jovanovich et al. control round per minute (RPM) or agitation timing but lacks fine trituration control whereas the current invention allows user selection of flow rate, volume per cycle, and number of triturations, enabling customized dissociation for different tissue types and experimental conditions.

The automated primary cells' triturator uses standard sterile pipettes with known bore sizes being inserted into tubes containing suspensions, enabling reproducibility and integration with existing lab workflows. In contrast, the invention of Jovanovich et al. requires custom hardware not easily adaptable to the standard lab protocols.

The invention of Jovanovich et al. is a bench-bound for general tissue homogenates and relies on disposable cartridges, whereas the automated primary cells' triturator (of the current invention) is portable, battery-operated, and compatible with sterile laminar hoods, making it suitable for both research and clinical settings where contamination control is essential.

Lastly, the automated primary cells' triturator uses two samples simultaneously with interchangeable pipettes providing higher efficiency and lab productivity while the invention of Jovanovich et al. uses single sample in enclosed cartridge.

The automated primary cells' triturator pertains to mechanical dissociation (trituration) of primary cells from tissues using a controlled, automated system tailored to biological and cellular integrity requirements, particularly for fragile cell types such as neurons while the invention of Poggel et al. (U.S. Ser. No. 10/287,543) relates to a syringe-based fluid handling system designed for microfluidic and biomedical workflows, emphasizing fluid movement and isn't suitable for fragile cells.

The automated primary cells' triturator is based on suction and dispensing tools with The automated primary cells' triturator is based on suction and dispensing tools with control of number of trituration cycles, flow rate, and aspirated volume while the invention of Poggel et al. involves syringe pump with cassettes, valves, and pressure sensor while the invention of Poggel et al. involves syringe pump with cassettes, valves, and pressure sensors.

The automated primary cells' triturator uses pipette-based mechanical trituration with adjustable flow rate, volume, and trituration cycles. Meanwhile, the invention of Poggel et al. employs pressure-driven syringe pumps with removable cassettes and feedback sensors.

The automated primary cells' triturator features an LCD interface for setting biological protocol parameters (number of trituration cycles, flow rate, and aspirated volume) while the invention of Poggel et al. is a programmable system using motor controls and valve feedback but not optimized for the isolation of fragile cells and is limited to fluid control.

The automated primary cells' triturator is portable, battery-operated device designed for use in sterile environments (e.g., laminar flow hoods). In contrast, the invention of Poggel et al. isn't described as portable or battery-powered. It is a desktop system.

The automated primary cells' triturator addresses standardized trituration force to prevent cell damage, simultaneous dual-sample processing and compatibility with variable bore pipettes in contrast to the invention of Poggel et al. which lacks these characteristics.

The automated primary cells' triturator uses pipettes with variable bore sizes while the invention of Poggel et al. uses fixed syringe cassettes.

The automated primary cells' triturator includes HEPA filter; designed for use in biosafety hoods in contrast to the invention of Poggel et al.

In conclusion, the primary cells' triturator is a machine that helps in the extraction of primary cells using a steady force and speed (flow rate) during trituration. It can decrease the efforts and time of researcher and allow flexibility in choosing the speed, suspension's volume and the number of trituration steps that can be used in the experiment. The apparatus can increase the number and quality of primary cells that survive in culture. Also, it helps in decreasing the costs of the experiment.

REFERENCES CITED

U.S. Patent Documents
U.S. Ser. No. 10/273,459B2, April 2019, Noggle et al.
U.S. Pat. No. 11,136,556 B2, October 2021, Noggle et al.
U.S. Pat. No. 5,691,208*, December 2023, Jovanovich et al.
US20220290094A1*, September 2022, Guest et al.
U.S. Pat. No. 5,691,208*, November 1997, Miltenyi et al.
U.S. Ser. No. 10/287,543*, May 2019, Poggel et al.
* Cited by the examiner
US20180305671A1, January 2021, Koehler et al.
U.S. Pat. No. 10,946,066, March 2021, Rafii et al.
US20080187519A1, August 2008, Sen et al.
U.S. Pat. No. 9,580,678 B2, February 2017, Haun et al.

International Applications

WO 2017/127921 A1, August 2017, Timmins et al.

OTHER REFERENCES

Shefer, G., Yablonka-Reuveni, Z. (2005). Isolation and culture of skeletal muscle Myofibers as a means to analyze satellite cells. Basic Cell Culture Protocols, 281-304.
Freshney (1987). Culture of Animal Cells. A Manual of Basic Techniques, 2d Ed., A. R. Liss, Inc., New York, Ch. 11 and 12.
Sahar Majdi Jaffal, Sawsan Atallah Oran, Mohammad Issa Alsalem, Belal Omar Al-Najjar (2021). Effect of Arbutus andrachne L. Methanolic Leaf Extract on The Function Of Transient receptor potential vanilloid 1: Experimental and Molecular Docking Studies (submitted article).
Ray, B., Chopra, N., Long, J. M., Lahiri, D. K. (2014). Human primary mixed brain cultures: Preparation, differentiation, characterization and application to neuroscience research. Molecular Brain, 7(1).
Sophia E. Black (2017). Effects of intracellular beta amyloid on mitochondria in triturated glial cells of *Gallus gallus*. Wheaton Journal of Neurobiology Research, 9: 1-10.

What is claimed:

1. An automated portable, lightweight primary cells' triturator comprising a machine configured to isolate and disperse primary cells from tissues comprising:
   a handle for easy transport;
   a housing made of a fireproof, waterproof, rust-proof interior surface and a heat-resistant, stain-resistant plastic exterior surface sterilizable with ethanol;
   a chamber holding a cell suspension, wherein the suspension's volume is adjustable;
   a high efficiency particulate air (HEPA) filter built into the machine to maintain sterility;
   a power system using either an electrical connection or a rechargeable battery housed in a waterproof compartment that can be charged using an electric plug or a portable adapter;
   a plurality of sterile disposable glass pipettes fixed to the top of the housing including one wide-bore pipette with a diameter of 1-1.5 mm for gross cell dissociation and one narrow-bore pipette with a diameter of 0.3-0.5 mm for fine dissociation and single cell release without damaging cells;
   sterile tubes fixed to a base of the machine, wherein each sterile tube is coupled to a perforated cap to prevent gas accumulation;
   a motorized suction-dispensing system configured to aspirate and dispense a cell suspension containing cells and media at a constant flow rate of 6.2-50 ml/see with the aid of a pulse wave modulation (PWM) high current motor speed controller (IC 555) connected to a power switch and suction tool aspirating media at a constant flow rate and a dispensing tool providing pressure that dispenses media into the sterile tubes;
   an outlet nozzle for air pressure regulation during operation;
   a user interface liquid crystal display (LCD) screen with touch-screen controls for indicating the battery charge-level and selecting trituration cycle count, suspension's volume and flow rate; and
   a heating element at the base of the machine to maintain cell temperature.

* * * * *